(12) United States Patent
Salvador et al.

(10) Patent No.: US 10,473,604 B2
(45) Date of Patent: Nov. 12, 2019

(54) METHOD OF DETERMINING DEFORMATION LOCATION

(71) Applicant: GM GLOBAL TECHNOLOGY OPERATIONS LLC, Detroit, MI (US)

(72) Inventors: James R. Salvador, Royal Oak, MI (US); Debejyo Chakraborty, Novi, MI (US); Leonid C. Lev, West Bloomfield, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 0 days.

(21) Appl. No.: 15/736,560

(22) PCT Filed: Apr. 29, 2016

(86) PCT No.: PCT/US2016/030034
§ 371 (c)(1),
(2) Date: Dec. 14, 2017

(87) PCT Pub. No.: WO2017/003553
PCT Pub. Date: Jan. 5, 2017

(65) Prior Publication Data
US 2018/0172613 A1 Jun. 21, 2018

Related U.S. Application Data

(60) Provisional application No. 62/186,568, filed on Jun. 30, 2015.

(51) Int. Cl.
*G01N 27/04* (2006.01)
*G01D 21/00* (2006.01)
(Continued)

(52) U.S. Cl.
CPC ............ *G01N 27/041* (2013.01); *C08L 23/06* (2013.01); *C08L 23/12* (2013.01); *C08L 33/12* (2013.01);
(Continued)

(58) Field of Classification Search
CPC ................................ G06F 3/0414; G06F 3/045
See application file for complete search history.

(56) References Cited

U.S. PATENT DOCUMENTS 4,940,959 A 7/1990 Zeller et al.
5,951,846 A 9/1999 Lewis et al.
(Continued)

FOREIGN PATENT DOCUMENTS

EP 0376632 A1 12/1989
EP 0376632 A1 7/1990
(Continued)

OTHER PUBLICATIONS

ISA KIPO, International Preliminary Report on Patentability issued in International Application No. PCT/US2016/030023, dated Jan. 11, 2018.
(Continued)

*Primary Examiner* — Noam Reisner
(74) *Attorney, Agent, or Firm* — Lorenz & Kopf, LLP (57) ABSTRACT

A number of variations may involve a method that may include providing a non-conductive layer. A conductive layer may be provided overlying the non-conductive layer with the conductive layer to form a sensor device. An opposition to electrical current through the conductive layer may be monitored. The location of a status of the non-conductive layer or of the conductive layer may be determined through a change in the opposition.

16 Claims, 3 Drawing Sheets

(51) Int. Cl.
*G01N 27/12* (2006.01)
*G01R 27/14* (2006.01)
*G01N 27/26* (2006.01)
*C08L 23/06* (2006.01)
*C08L 23/12* (2006.01)
*C08L 33/12* (2006.01)

(52) U.S. Cl.
CPC ............ *G01D 21/00* (2013.01); *G01N 27/04* (2013.01); *G01N 27/125* (2013.01); *G01N 27/26* (2013.01); *G01R 27/14* (2013.01)

(56) References Cited

U.S. PATENT DOCUMENTS

| | | | |
|---|---|---|---|
| 6,093,308 | A | 7/2000 | Lewis et al. |
| 6,902,701 | B1 | 6/2005 | Hughes et al. |
| 2001/0048139 | A1 | 12/2001 | Aigner et al. |
| 2007/0125150 | A1 | 6/2007 | Stievater |
| 2007/0273394 | A1 | 11/2007 | Tanner |
| 2008/0127739 | A1 | 6/2008 | DeAngelis et al. |
| 2008/0150556 | A1 | 6/2008 | Han |
| 2008/0289426 | A1 | 11/2008 | Kearns et al. |
| 2008/0319682 | A1 | 12/2008 | Holand |
| 2009/0241681 | A1* | 10/2009 | Machauf ............... B81B 3/0021 73/777 |
| 2009/0251155 | A1 | 10/2009 | Wang et al. |
| 2010/0160755 | A1 | 6/2010 | Oviatt et al. |
| 2010/0301197 | A1 | 12/2010 | Boyle |
| 2011/0210751 | A1 | 9/2011 | Hong |
| 2012/0071362 | A1 | 3/2012 | Nhan et al. |
| 2012/0120009 | A1 | 5/2012 | Lussey |
| 2012/0292255 | A1 | 11/2012 | Nikoobakht |
| 2012/0315623 | A1 | 12/2012 | Alocilja et al. |
| 2015/0082920 | A1 | 3/2015 | Haick et al. |
| 2015/0219581 | A1 | 8/2015 | Santangelo |
| 2015/0276883 | A1 | 10/2015 | Masias |
| 2016/0103545 | A1* | 4/2016 | Filiz ..................... G01L 1/18 345/174 |
| 2016/0262670 | A1 | 9/2016 | Wasson |
| 2016/0334912 | A1* | 11/2016 | Protasio Ribeiro ... G06F 3/0414 |

FOREIGN PATENT DOCUMENTS

| | | |
|---|---|---|
| EP | 209109 A1 | 11/2007 |
| EP | 2128598 A1 | 5/2008 |
| WO | 2005039012 A2 | 4/2005 |
| WO | 2014043418 A1 | 3/2014 |

OTHER PUBLICATIONS

ISA KIPO, International Preliminary Report on Patentability issued in International Application No. PCT/US2016/030029, dated Jan. 11, 2018.

ISA KIPO, International Preliminary Report on Patentability issued in International Application No. PCT/US2016/030034, dated Jan. 11, 2018.

ISA KIPO, International Search Report and Written Opinion issued in International Application No. PCT/US2016/030023, dated Aug. 17, 2016.

ISA, KIPO, International Search Report and Written Opinion issued in International Application No. PCT/US2016/030029, dated Aug. 17, 2016.

ISA KIPO, International Search Report and Written Opinion issued in International Application No. PCT/US2016/030034, dated Aug. 17, 2016.

* cited by examiner

METHOD OF DETERMINING DEFORMATION LOCATION

CROSS REFERENCE TO RELATED APPLICATION

This application is a U.S. National-Stage entry under 35 U.S.C. § 371 based on International Application No. PCT/US16/30034, filed Apr. 29, 2016, which was published under PCT Article 21(2) and, claims benefit of U.S. Provisional Application No. 62/186,568 filed Jun. 30, 2015.

TECHNICAL FIELD

The field to which the disclosure generally relates includes sensor devices and methods of making them and using them to measure variables.

BACKGROUND

In a number of variations, sensor devices may be used to measure environmental conditions or variables pertaining to components.

SUMMARY OF ILLUSTRATIVE VARIATIONS

A number of variations may involve a method that may include providing a non-conductive layer. A conductive layer may be provided overlying the non-conductive layer with the conductive layer to form a sensor device. An opposition to electrical current through the conductive layer may be monitored. The location of a status of the non-conductive layer or of the conductive layer may be determined through a change in the opposition.

A number of other variations may involve a method and may include providing a non-conductive layer. The non-conductive layer may be positioned to monitor a potential deformation. A conductive layer may be provided, overlying at least a part of the non-conductive layer with the conductive layer to form a sensor device. An occurrence of the deformation may be determined by monitoring the conductive layer.

A number of additional variations may involve a method that may include providing a substrate. A sensor device may be coupled to the substrate and may include a non-conductive layer and a conductive layer overlying the non-conductive layer. The sensor device may be constructed and arranged to measure or monitor at least one variable in the substrate, or a change in an opposition to current in the conductive layer to provide measurement or monitoring of the at least one variable based on at least one calculation.

Other illustrative variations within the scope of the invention will become apparent from the detailed description provided hereinafter. It should be understood that the detailed description and specific examples, while disclosing variations within the scope of the invention, are intended for purposes of illustration only and are not intended to limit the scope of the invention.

BRIEF DESCRIPTION OF THE DRAWINGS

Select examples of variations within the scope of the invention will become more fully understood from the detailed description and the accompanying drawings, wherein.

DETAILED DESCRIPTION OF ILLUSTRATIVE VARIATIONS

The following description of the variations is merely illustrative in nature and is in no way intended to limit the scope of the invention, its application, or uses.

Figure 1:
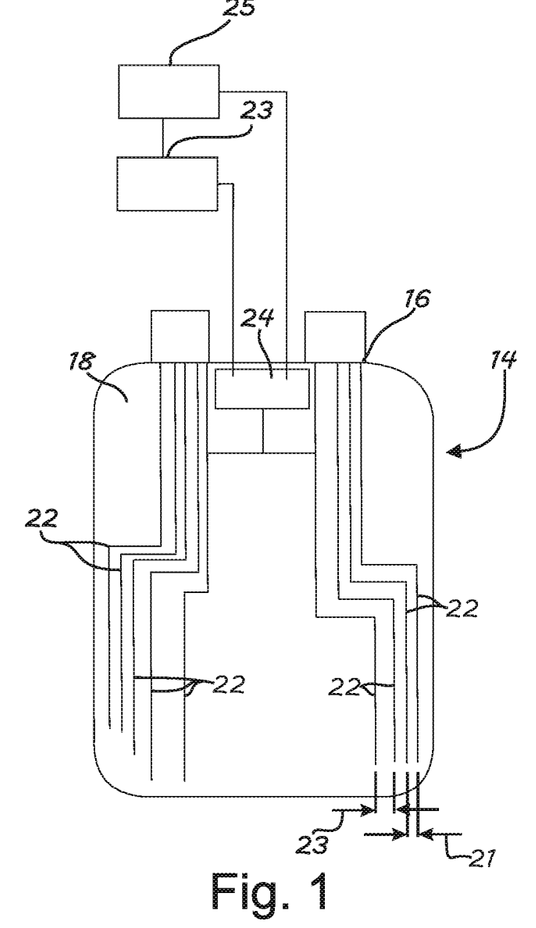
FIG. 1 illustrates a product according to a number of variations.
Figure 2:
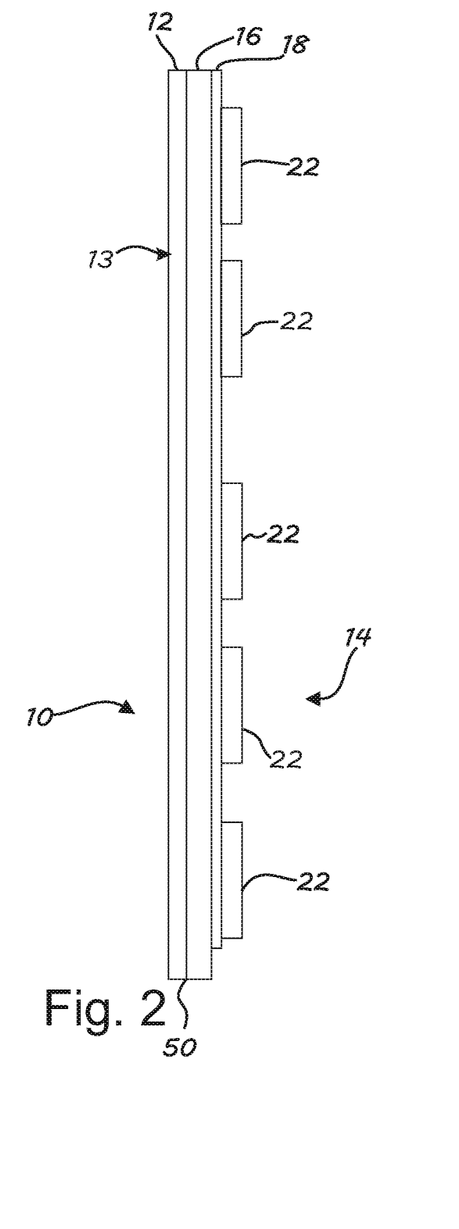
FIG. 2 illustrates a product according to a number of variations.

FIGS. 1 and 2 show a product 10 according to a number of variations. In a number of variations, the product 10 may include a substrate 12. In a number of variations, the product 10 may include a sensor device 14. The sensor device 14 may include a non-conductive layer 16. The sensor device 14 may include a conductive layer 18. The conductive layer 18 may overlie the non-conductive layer 16. In a number of variations, the sensor device 14 may overlie, or may otherwise be in physical contact with, the substrate 12. In a number of variations, the sensor device 14 may be in close proximity to the substrate 12 or at any location where sensing is desired. In a number of variations, the sensor device 14 may be constructed and arranged to measure or monitor at least one variable. The variable may involve a physical property such as temperature, pressure (strain), deformation, or another property, or may involve detection, identification, classification, tracking, or other characteristics of a property. The variable may involve concentration, quantity, rate, time or another characteristic of a compound, such as volatile organic compound concentration. The variable may involve a status of a device or environment such as state of charge, or state of health of the substrate 12, depletion status, diagnosis properties, or other variables indicative of status. In a number of variations, the substrate 12 may include a two dimensional surface. In a number of variations, the substrate 12 may include a three dimensional surface. In a number of variations, the sensor device 14 may be used to cover the substrate 12 surface area at a percentage from 0 to 100%. In a number of variations, a plurality of sensor devices 14 may be used to cover the substrate 12 surface area at a percentage from 0 to 100%. In a number of variations, the substrate 12 may include a battery or battery exterior surface. In a number of variations the substrate 12 may include any host for which monitoring with the sensor device 14 is desirable. In a number of variations, the operation of the battery may be controlled via a battery control module (BCM) 23. In a number of variations, the substrate 12 may include a lithium ion battery 13 including, but not limited to, the battery pouch, housing, or casing. In a number of variations, the substrate 12 may include a cooling fin, cooling fin exterior, or surface of the battery 13. In a number of variations, the substrate 12 may include a battery or cooling fin for a vehicle including but not limited to, a motor vehicle, watercraft, spacecraft, aircraft, or may be another type. In a number of variations, the sensor device 14 may include at least one lead 22. In a number of variations the sensor device 14 may comprise the non-conductive layer 16, the conductive layer 18 and the lead 22.

Resistance and impedance may be generally referred to an opposition to the passage of an applied current from a DC or AC source, through an area of interest as detected through the one or more leads 22. In a number of variations, the sensor device 14 may include a data acquisition module (DAQ) 24. In a number of variations, the sensor device 14 may be electrically isolated from the substrate 12. In a number of variations, the sensor device 14 or data acquisition module 24 may be electrically coupled to an electronic control module (ECM) 25, which may be a controller for processing information, and may be included in a mobile or stationary host. As used herein, the term "electrically coupled" may mean possessing the ability to transfer electrons or electric signals between the at least two components. As used herein, the term "electrically coupled" relationship may include a conducting wire or may include wireless connection. In a number of variations, the at least one variable may be measured via inputs of at least one of deformation of the non-conductive layer 16 or substrate 12, or change in opposition to current of the conductive layer 18 through one or more areas of interest, which may involve at least one calculation, such as determining the change, rate of change, or comparison with a threshold. In a number of variations, the sensor device 14 may be physically attached to the substrate 12 through an attachment 50. In a number of variations, the substrate 12 could be an electrical component. In a number of variations, the substrate 12 could be a foodstuff packaging component. In a number of variations, the substrate 12 could be a fiber optic component.

In a number of variations, the non-conductive layer 16 may include a polymeric material. The non-conductive layer 16 may comprise a polymer including, but not limited to, Acrylonitrile butadiene styrene (ABS), Polymethyl Methacrylate (PMMA), Celluloid, Cellulose acetate, Cycloolefin Copolymer (COC), Ethylene-Vinyl Acetate (EVA), Ethylene vinyl alcohol (EVOH), Fluoroplastics (including PTFE, FEP, PFA, CTFE, ECTFE, ETFE) Ionomers, Kydex™, a trademarked acrylic/PVC alloy, Liquid Crystal Polymer (LCP), Polyacetal (POM or Acetal), Polyacrylates (Acrylic), Polyacrylonitrile (PAN or Acrylonitrile), Polyamide (PA or Nylon), Polyamide-imide (PAI), Polyaryletherketone (PAEK or Ketone), Polybutadiene (PBD), Polybutylene (PB), Polybutylene terephthalate (PBT), Polycaprolactone (PCL), Polychlorotrifluoroethylene (PCTFE), Polyethylene terephthalate (PET), Polycyclohexylene dimethylene terephthalate (PCT), Polycarbonate (PC), Polyhydroxyalkanoates (PHAs), Polyketone (PK), Polyester, Polyetheretherketone (PEEK), Polyetherketoneketone (PEKK), Polyetherimide (PEI), Polyethersulfone (PES), Polysulfone, Polyethylenechlorinates (PEC), Polyimide (PI), Polylactic acid (PLA), Polymethylpentene (PMP), Polyphenylene oxide (PPO), Polyphenylene sulfide (PPS), Polyphthalamide (PPA), Polystyrene (PS), Polysulfone (PSU), Polytrimethylene terephthalate (PTT), Polyurethane (PU), Polyvinyl acetate (PVA), Polyvinyl chloride (PVC), Polyvinylidene chloride (PVDC), Styrene-acrylonitrile (SAN), polycarbonate+ acrylonitrile butadiene styrene mix (ABS+PC), Polypropylene (PP) (including, but not limited to, impact, random, and homo), Polyethylene (PE) (including, but not limited to, linear low density, linear high density), combinations or blends in any amount thereof, or may be another type. In a number of variations, the non-conductive layer 16 may be a combination of the above polymers in any amount or concentration. In a number of variations, the non-conductive layer 16 may include a composite layer comprising several layers of the materials listed. In a number of variations, the non-conductive layer 16 may be formed via a method including, but not limited to, injection molding, extrusion molding, structural foam, vacuum forming, extrusion blow molding, a hand lay-up operation, a spray lay-up operation, a pultrusion operation, a chopped strand mat, vacuum bag molding, pressure bag molding, autoclave molding, resin transfer molding, vacuum assisted resin transfer molding, bladder molding, compression molding, mandrel wrapping, wet layup, chopper gun, filament winding, melting, staple fiber, continuous filament, lamination, or may be formed another way.

In a number of variations, the conductive layer 18 may include a metallic or semi-metallic material. In a number of variations, the conductive layer 18 may include a metal including, but not limited to, plastic steel, stainless steel, copper, nickel, tin, gold, silver, molybdenum, palladium, tungsten, graphite, zinc, iron, bronze, aluminum, titanium, platinum, silicide, or may be another type), metallic alloys, graphite, graphene, another form of carbon, combinations thereof, or may be another type. In a number of variations the conductive layer may include a non-metal material that conducts electric current sufficient to measure changes in impedance or resistance. In a number of variations, the conductive layer 18 may be a combination of the materials in any amount or concentration. In a number of variations, the conductive layer 18 may include a composite layer comprising several layers of the materials. In a number of variations, the conductive layer 18 may be formed on or overlying the non-conductive layer 16 via a method including, but not limited to, inkjet/laser printing, 3-D printing, casting, extrusion, forging, plating (electroless, electro), plasma spraying, aerosol spraying, thermal spraying, dip coating, roll-to-roll coating, spin coating, spray coating, chemical solution deposition, thermal evaporation, pulsed laser deposition, cathodic arc deposition, or known etching techniques (i.e. sputter, Chemical Vapor Deposition, Physical Vapor Disposition, Atomic Vapor Disposition, ALD, or combination of deposition and thermal growth), conversion coating, ion beam mixing, thin film printing, or may be formed another way.

In a number of variations, the at least one lead 22 may include a conductor such as a metal material, and may be used to measure resistance or impedance in an area of interest. In a number of variations, the at least one lead 22 may include a metal including, but not limited to, plastic steel, stainless steel, copper, nickel, tin, gold, silver, molybdenum, palladium, tungsten, graphite, zinc, iron, bronze, aluminum, titanium, platinum, silicide, or may be another type), metallic alloys, combinations thereof, or may be another type of electrical conducting material. In a number of variations, the at least one lead 22 may be a combination of materials in any amount or concentration. In a number of variations, the at least one lead 22 may include a composite layer comprising several layers of materials. In a number of variations, the at least one lead 22 may be formed on or overlying the conductive layer 18, or otherwise in contact therewith (such as being formed on the non-conductive layer 16), via a method including, but not limited to, inkjet/laser printing, 3-D printing, casting, extrusion, forging, plating (electroless, electro), plasma spraying, thermal spraying, dip coating, roll-to-roll coating, spin coating, spray coating, chemical solution deposition, thermal evaporation, pulsed laser deposition, cathodic arc deposition, or known etching techniques (i.e. sputter, Chemical Vapor Deposition, Physical Vapor Disposition, Atomic Vapor Disposition, ALD, or combination of deposition and thermal growth), conversion coating, ion beam mixing, thin film printing, or may be formed another way. In a number of variations, the at least one lead 22 may be attached to the conductive layer 18, or the non-conductive layer 16, through an adhesive comprising at least one of, silver paste, acrylonitrile, cyanoacrylate, acrylic, resorcinol glue, epoxy resin, epoxy putty, ethylene-vinyl acetate, phenol formaldehyde resin, polyamide, polyester, polyethylene, polypropylene, polysulfides, polyurethane, polyvinyl acetate, polyvinyl alcohol, polyvinyl chloride, polyvinyl chloride emulsion, polyvinylpyrrolidone, rubber cement, silicone, combinations thereof, or may be another type. The contact between the impedance leads and the conductive surface may be ohmic or nearly ohmic. A conductive adhesive may be used or a metal with direct contact to the conducting layer may be applied by printing, CVD, PVD, or another process. In a number of variations as shown in FIG. 1, the leads may be provided individually, or in pairs with different spacing. For example a first pair may have a spacing that represents a distance 21 between the leads 22 and a second pair may have a second spacing of a distance 23 that may have a greater distance between the leads 22. The distances 21, 23 may span areas of interest for monitoring changes in opposition to current. In a number of variations providing different distances between the pairs of leads enables tailoring the sensitivity of the sensor device 14. In a number of variations providing different distances 21, 23 may provide indications of different threshold concentrations of an analyte. For example, a first concentration may report through the distance 21 and not through the distance 23, and a second greater concentration may report through the distance 21 and the distance 23. A similar result may be achieved by varying the contact resistance between individual leads 22 and the conductive layer 18.

In a number of variations, the sensor device 14 may be physically attached to the substrate 12 via an attachment 50. In a number of variations, the attachment 50 may include an adhesive including at least one of, acrylonitrile, cyanoacrylate, acrylic, resorcinol glue, epoxy resin, epoxy putty, ethylene-vinyl acetate, phenol formaldehyde resin, polyamide, polyester, polyethylene, polypropylene, polysulfides, polyurethane, polyvinyl acetate, polyvinyl alcohol, polyvinyl chloride, polyvinyl chloride emulsion, polyvinylpyrrolidone, rubber cement, UV-cure, silicone, combinations thereof, or may be another type.

Figure 3:
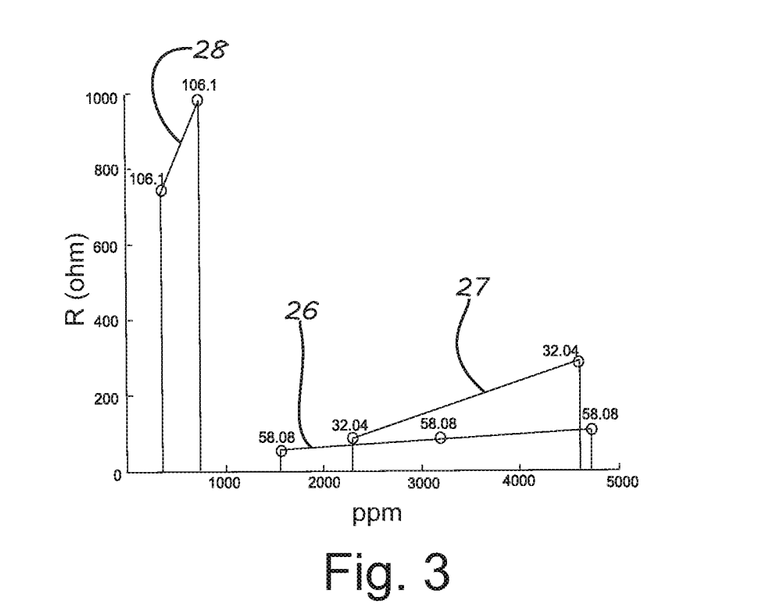
FIG. 3 illustrates a graph of volatile organic compounds in relation to measured resistance versus concentration of a product according to a number of variations.

In a number of variations, the sensor device 14, non-conductive layer 16, and/or conductive layer 18 may operate as or include a strain gauge. In a number of variations, the sensor device 14, non-conductive layer 16, and/or conductive layer 18 may be used to operate as a strain gauge to measure state of charge (SOC) or state of health (SOH) of a battery, or other status of the substrate 12, by measuring deformation of the substrate 12 and/or non-conductive layer 16, or change in resistance of the conductive layer 18 through at least one calculation. In a number of variations, SOC or SOH calculation may include several percent changes in resistance over the charge window and larger variations for lower state of health. Thermal expansion of the non-conductive layer 16 and conductive layer 18 may be compensated through variations in sensor layout to discern expansion due to the monitored factor(s). Multiple leads 22 may be used to pinpoint a location of deformation, wherein different changes may be detected through different leads at positioned at known locations In a number of variations, the sensor device 14, non-conductive layer 16, and/or conductive layer 18 may be used to operate as a strain gauge to measure compounds such as volatile organic compounds (VOC's) in vapor state by measuring deformation of the substrate 12 and/or non-conductive layer 16, or change in resistance of the conductive layer 18 through at least one calculation. In a number of variations, the VOC's may include, but are not limited to, aromatic hydrocarbons, octane, ketones, or aldehydes, glycols, or may be another compound. In a number of variations, resistance changes comparable to SOC changes, though with a significantly different temporal response, may be registered for VOC sensing. In a number of variations, the presence of VOC's may indicate electrolyte decomposition within the substrate 12 or battery or leaks within the substrate 12 as a pouch, casing or housing. In a number of variations, electrolyte decomposition may decrease the life cycle of the battery. FIG. 3 illustrates a relation of the VOC concentration to resistance measured in the conductive layer according to a number of variations. The resistance change in Ohms of the sensor device 14 is shown on the vertical axis as a function of analyte vapor concentrations presented in parts per million on the horizontal axis. Proportional responses are demonstrated for acetone at curve 26, methanol at curve 27 and xylene at curve 28. In a number of variations, the non-conductive coating 16 and/or conductive coating of the sensor device 14 may be used to operate as a PTC thermocouple to measure temperature of the substrate 12 or the area in close proximity to the substrate 12 through at least one calculation. In a number of variations, the pressure calculation may include several percent change in the resistance of the conductive coating. In a number of variations, the non-conductive coating 16 and/or conductive coating of the sensor device 14 may be used to operate as a PTC thermocouple to measure temperature of the substrate 12 or the area in close proximity to the substrate 12 through at least one calculation. In a number of variations, the pressure calculation may include a lower response for PTC by several fractions of a percent. In a number of variations, where the substrate 12 is a cooling fin, the non-conductive coating 16 and/or conductive coating of the sensor device 14 may be used to operate as a flowmeter to measure flowrate of the coolant surrounding the substrate 12 or the area in close proximity to the substrate 12 by measuring deformation of the substrate 12 and/or non-conductive layer 16, or change in resistance of the conductive layer 18 through at least one calculation. In a number of variations, the flowrate calculation may include several percent to tens of percent change in the resistance of the conductive coating. In a number of variations, the sensor device 14 may cover the entirety of the substrate 12 and act as a grid-like system of interconnected sensor devices 14 to provide inputs to determine variables at a number of locations on or in close proximity to the substrate 12 to provide local and overall variable (including, but not limited to, temperature, pressure (strain), volatile organic compound concentration, state of charge, or state of health of the substrate 12) measurement and monitoring through at least one calculation. In a number of variations the sensor device 14 provides the ability to detect VOCs in low concentrations through deformation induced by VOC absorption in an electrically insulating polymer—non-conducting layer 16. The deformation may be detected by measuring changes in resistance or impedance of the conductive coating and/or of the non-conducting layer 16. Direct current may be used, and alternating current is and alternative. The polymer non-conducting layer 16 may absorb the organic gas phase compounds causing micro swelling and elastic deformation. The resulting strain may modify the conduction paths of the conductive layer 18 resulting in a measurable resistance or impedance change. The ability to discriminate to analytes of choice, in the sensor device 14 with a rapid response, reversibility and high sensitivity is provided.

In a number of variations, placement of a plurality of sensor devices 14 onto various locations on or in close proximity to a substrate 12 may decouple the deformation measurements of the substrate 12 and/or non-conductive layer 16 to provide more accurate measurement and monitoring on deformation related to SOC or SOH versus deformation related to the presence of VOC's. Comparable resistance changes may be indicated by all three but all may have a different temporal response. SOC changes may be cyclical in nature, SOH changes may be persistent, and VOC induced changes may be rapid and may be sustained. In a number of variations, this may allow the sensor device 14 or plurality of sensor devices 14 to measure the presence of VOC's in relation to the substrate 12 independent of the state of charge or state of health measurements of the substrate 12 via a calculation and may be measured independent of SOC or SOH measurement through the use of the PTC thermocouple.

Figure 4:
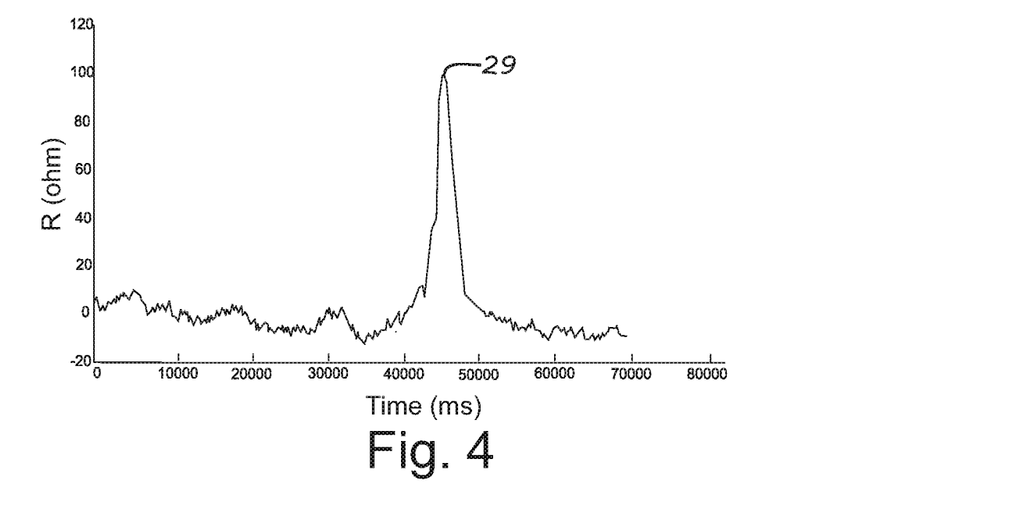
FIG. 4 illustrates a graph of response to volatile organic compounds in relation to measured resistance versus time of a product according to a number of variations.

In a number of variations, spikes in the measured resistance, as illustrated as spike 29 in FIG. 4 for example, may indicate a change or increase in presence of VOC's while rate of change in the resistance may indicate a change in the state of charge or state of health of the cell. SOH changes may be persistent and may result in sustained higher resistance or lower than expected resistances over the SOC window. In a number of variations, placement of a plurality of sensor devices 14 onto various locations on or in close proximity to a substrate 12 may decouple the deformation measurements of the substrate 12 and/or non-conductive layer 16 to provide more accurate measurement and monitoring on deformation related to SOC or SOH versus deformation related to the temperature or pressure changes. Modulation of sensor probe spacing may allow for a linear regression response for CTE while deformation due to SOC and SOH changes may represent significant departures from the nonlinear behavior over the plurality of probe spacing. In a number of variations, temperature or pressure may be indicated through deformation measurements of the substrate 12 and/or source generating the VOC. For example, the sensor device 14 may be exposed to acetone introduced to the sensing device 14 in the presence of air flow. A measured resistance of greater than the baseline of approximately 10 ohms may indicate the presence of acetone in the environment, while the rapid change from the baseline to the peak 29 may indicate an underlying change in the operation being monitored, where the changes results in the generation or release of additional acetone from a norm. As demonstrated, the sensor device 14 responds to the introduction of analytes quickly and returns to the baseline resistance after the exposure demonstrating a rapid and reversible response. As can be seen the signal to noise of the response is very good and the response nearly instantaneous. Return to the base line within seconds demonstrates that very small and quick changes in environmental quality can be detected readily.

With reference again to FIG. 1, in a number of variations, the DAQ 24 or the ECM 25 may receive and process input from at least one sensor device 14 in light of stored instructions and/or data, determine a variable through at least one calculation, and transmit output signals to various receptors or actuators, including, but not limited to, the substrate 12, the battery, the cooling fin, the battery control module (BCM) 23 or vehicle itself may include, for example, an electrical circuit, an electronic circuit or chip, and/or a computer. In an illustrative computer variation, the data acquisition module (DAQ) 24, battery control module (BCM) 23, or electronic control module (ECM) 25 generally may include one or more processors, or memory storage units that may be coupled to the processor(s), and one or more interfaces electrically coupling the processor(s) to one or more other devices, including at least one of the other of the data acquisition module (DAQ) 24, battery control module (BCM) 23, or electronic control module (ECM) 25, or to the at least one sensor device 14, or to a different component of a vehicle. The processor(s) and other powered system devices (including at least one of the other of the data acquisition module (DAQ) 24, battery control module (BCM) 23, electronic control module (ECM) 25, or to the at least one sensor device 14) may be supplied with electricity by a power supply, for example, a generated and distributed power source, the battery 13 itself, other fuel cells, a vehicle engine, other vehicle power component, or other source. The processor(s) may execute instructions or calculations that provide at least some of the functionality for the sensor device 14 and methods 800, 900. As used herein, the term instructions may include, for example, control logic, computer software and/or firmware, programmable instructions, or other suitable instructions. The processor may include, for example, one or more microprocessors, microcontrollers, application specific integrated circuits, programmable logic devices, field programmable gate arrays, and/or any other suitable type of electronic processing device(s).

Also, in a number of variations, the data acquisition module (DAQ) 24, battery control module (BCM) 23, or electronic control module (ECM) 25, may be configured to provide storage for data received by or loaded to the at least one of the other of the data acquisition module (DAQ) 24, battery control module (BCM) 23, or electronic control module (ECM) 25, or to the at least one sensor device 14, or to a different component of a vehicle, or the like, for processor-executable instructions or calculations. The data, calculations, and/or instructions may be stored, for example, as look-up tables, formulas, algorithms, maps, models, and/or any other suitable format. The memory may include, for example, RAM, ROM, EPROM, and/or any other suitable type of storage article and/or device.

In a number of variations, the interfaces may include, for example, analog/digital or digital/analog converters, signal conditioners, amplifiers, filters, other electronic devices or software modules, and/or any other suitable interfaces. The interfaces may conform to, for example, RS-232, parallel, small computer system interface, universal serial bus, CAN, MOST, LIN, FlexRay, and/or any other suitable protocol(s). The interfaces may include circuits, software, firmware, or any other device to assist or enable the data acquisition module (DAQ) 24, battery control module (BCM) 23, or electronic control module (ECM) 25, in communicating with other devices.

In a number of variations, the methods or parts thereof may be implemented in a computer program product including instructions or calculations carried on a computer readable medium for use by one or more processors to implement one or more of the method steps or instructions. The computer program product may include one or more software programs comprised of program instructions in source code, object code, executable code or other formats; one or more firmware programs; or hardware description language (HDL) files; and any program related data. The data may include data structures, look-up tables, or data in any other suitable format. The program instructions may include program modules, routines, programs, objects, components, and/or the like. The computer program may be executed on one processor or on multiple processors in communication with one another.

In a number of variations, the program(s) can be embodied on computer readable media, which can include one or more storage devices, articles of manufacture, or the like. Illustrative computer readable media include computer system memory, e.g. RAM (random access memory), ROM (read only memory); semiconductor memory, e.g. EPROM (erasable, programmable ROM), EEPROM (electrically erasable, programmable ROM), flash memory; magnetic or optical disks or tapes; and/or the like. The computer readable medium also may include computer to computer connections, for example, when data may be transferred or provided over a network or another communications connection (either wired, wireless, or a combination thereof). Any combination(s) of the above examples is also included within the scope of the computer-readable media. It is therefore to be understood that the method may be at least partially performed by any electronic articles and/or devices capable of executing instructions corresponding to one or more steps of the disclosed methods.

Figure 5:
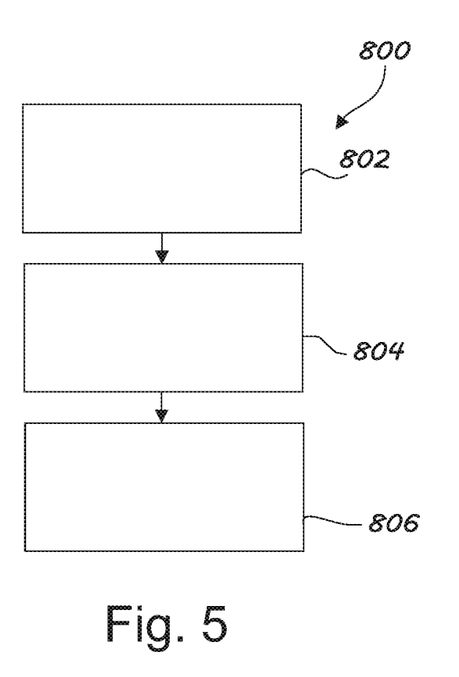
FIG. 5 illustrates methods according to a number of variations.
Figure 6:
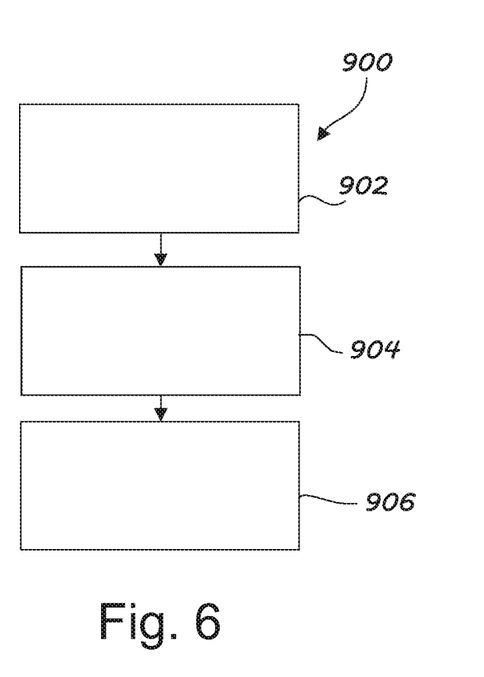
FIG. 6 illustrates methods according to a number of variations.

In a number of variations, as shown in FIG. 5, a method 800 is shown. In a number of variations, the method 800 may include a step 802 of providing a substrate 12. The method 800 further includes step 804 of providing a non-conductive layer 16 and overlying the substrate 12 with the non-conductive layer 16, or mounting the non-conductive layer 16 on the substrate 12. The method 800 may further include step 806 of providing a conductive layer 18 and overlying the non-conductive layer 16 with the conductive layer 18 to form a sensor device 14 constructed and arranged to measure or monitor at least one variable comprising at least one of temperature, pressure (strain), volatile organic compound concentration, state of charge, or state of health of the substrate 12, or the environment around the non-conductive layer 16. In a number of variations, as shown in FIG. 6, a method 900 is shown. The method 900 may include a step 902 of providing a substrate 12. The method 900 may further include step 904 of providing a sensor device 14 electronically coupled to the substrate 12 comprising a non-conductive layer 16 and a conductive layer 18 overlying the non-conductive layer 16 constructed and arranged to measure or monitor at least one variable comprising at least one of temperature, pressure (strain), volatile organic compound concentration, state of charge, or state of health of a substrate 12. The method 900 further includes step 906 of determining at least one of deformation of the non-conductive layer 16 or the substrate 12, or change in resistance of the conductive layer 18 to provide measurement or monitoring of the at least one variable based on at least one calculation. In a number of variations the lead(s) 22 may be connected to a power source, such as the battery 13. In a number of variations the lead(s) 22 may be provided in any manner to be electrically coupled to measure resistance or impedance in the conductive layer 18. In a number of variations the lead(s) 22 may be provided in differently spaced pairs. The methods 800, 900 may include providing a mechanism to monitor the response of the non-conductive layer 16, which may include providing the DAQ 24. In a number of variations the DAQ 24 may be connected with the lead(s) 22 to collect information. In a number of variations the lead(s) 22 may be connected directly to the ECM 25 to collect information. In a number of variations the DAQ 24 may monitor for resistance or impedance changes between a pair of leads 22. The methods 800, 900 may further include a step of determining a deformation of the non-conductive layer 16 by monitoring for a change in resistance between the lead(s) 22 to provide measurement or monitoring of a VOC in the environment surrounding the sensing device 14.

In a number of variations the methods 800, 900 may include determining the type of VOC sensed, such as by comparing the magnitude and/or the rate of the resistance change to known resistance changes for different types of VOCs, such as through a lookup table reference. In a number of variations the methods 800, 900 may include determining the concentration of VOC sensed, such as by comparing the magnitude of the resistance change to known resistance changes for different types of VOCs, such as through a lookup table reference. In a number of variations the methods 800, 900 may include monitoring for a change in an operation or an environment, where the changes results in the generation or release of additional VOC. For example, the normal presence of a varying amount of analyte may be accompanied by a rate of change indicative of an abnormal event. In a number of variations the methods 800, 900 may include determining the rise time between a baseline and a peak 29, and may include determining the magnitude of the peak 29 to determine the type of VOC sensed based its molecular weight. In a number of variations, the methods 800, 900 may use the non-conductive layer 16 and/or conductive layer 18 of the sensor device 14 to operate as a PTC thermocouple to measuring temperature of a substrate to which the sensor device 14 may be mounted or the area in close proximity to the sensor device 14 through at least one calculation. In a number of variations, the methods 800, 900 may include applying the sensor device 14 to cover relevant parts of the substrate 12 to which it may be mounted and may act as a grid-like system of interconnected sensor devices 14 to provide inputs to determine variables at a number of locations to provide local and overall variable (including, but not limited to, temperature, pressure, deformation, or volatile organic compound concentration), measurement and monitoring through at least one calculation. In a number of variations the sensor device may monitor for degradation of a substrate, such as a battery or welding electrodes by monitoring for the presence of VOCs.

As detailed above, the sensor device 14 may have multiple advantages including superior long term stability of the sensor since the polymer's chemical reactivity to the ambient environment is decoupled from the transduction mechanism through inclusion of the conductive layer 18, a faster response, and a higher degree reversibility since the transduced signal does not rely on a chemical interaction between the polymer and analyte. Use of the non-conducting layer 16 supports performance without a need to be shielded the sensor device 14 from water and oxygen since the polymer will not degrade over time. The sensor device 14 may be used for analyte detection, identification, classification, and/or tracking through a polymer non-conducting layer 16 with conductive layer 18 that may be provided as a coating on the non-conducting layer 16. Electrical resistance or impedance changes may be used for analyte classification. Signal processing for the detection, identification, classification and/or tracking of a narrow band of likely analyte. Tuning sensitivity for a specific analyte may be accomplished by altering the composition of the non-conductive layer 16. For example, PMMA may be used due to its sensitivity to polar compounds while PE or PP may be used due to their sensitivity to nonpolar species. An array of sensors with unique response to individual analyte may be used for classifications. Examples of uses of the products and methods described herein may include food quality inspection, pharmaceutical processing, chemical synthesis, beverage processing, monitoring for health purposes, cosmetic production, manufacturing plant monitoring, vehicle interior air quality, residential air evaluation, vehicle shed testing, or any application where the monitoring, detection, identification, classification, and/or tracking of analytes is desired.

The following description of variants is only illustrative of components, elements, acts, product and methods considered to be within the scope of the invention and are not in any way intended to limit such scope by what is specifically disclosed or not expressly set forth. The components, elements, acts, product and methods as described herein may be combined and rearranged other than as expressly described herein and still are considered to be within the scope of the invention.

Variation 1 may involve a method that may include providing a non-conductive layer. A conductive layer may be provided overlying the non-conductive layer with the conductive layer to form a sensor device. An opposition to electrical current through the conductive layer may be monitored. The location of a status of the non-conductive layer or of the conductive layer may be determined through a change in the opposition.

Variation 2 may include the method of variation 1 and may include providing a number of leads electrically coupled with the conductive layer.

Variation 3 may include the method of variation 2 and may include passing the electrical current through the leads and into the conductive layer. Monitoring may be conducted for the change in the opposition to the current through the conductive layer.

Variation 4 may include the method of variation 1 and may include providing a substrate. The non-conductive layer may be positioned relative to a substrate. The substrate may be monitored with the sensor device. The status of the substrate may be determined through the changes in the opposition.

Variation 5 may include the method of variation 1 wherein determining the status of the substrate may include determining a deformation of the substrate.

Variation 6 may include the method of variation 5 and may include positioning the sensor device in contact with the substrate.

Variation 7 may include the method of variation 6 and may include providing an array of sensor devices. The array may be monitored and differences in the opposition at individuals of the sensor devices in the array may be evaluated to determine a location of the deformation.

Variation 8 may include the method of variation 1 and may include providing a number of leads each electrically coupled with the conductive layer in various locations. The location of a change in the status may be determined by measuring the opposition to current through the conductive layer from each of the number of leads.

Variation 9 may include the method of variation 1 and may include measuring the opposition to the current; and may include comparing at least one of a magnitude of a change in the opposition, or a rate of change of the opposition, to known values to determine a magnitude of the deformation.

Variation 10 may include the method of variation 1 and may include monitoring temperature; and correcting the opposition for the monitored temperature change.

Variation 11 may involve a method and may include providing a non-conductive layer. The non-conductive layer may be positioned to monitor a potential deformation. A conductive layer may be provided, overlying at least a part of the non-conductive layer with the conductive layer to form a sensor device. An occurrence of the deformation may be determined by monitoring the conductive layer.

Variation 12 may include the method of variation 11 and may include identifying multiple changes in the opposition; and determining a location of the deformation by comparing the multiple changes.

Variation 13 may include the method of variation 11 and may include providing a number of leads electrically coupled with the conductive layer. Electrical current may be passed through the leads and into the conductive layer. Monitoring may be conducted for changes in an opposition to the current passing through the conductive layer.

Variation 14 may include the method of variation 13 and may include determining a location of the deformation, including providing a variation between individuals of the leads and the conductive layer. The opposition to current through the conductive layer may be measured from each of the number of leads. The measurements may be compared to determine the location.

Variation 15 may include the method of variation 11 and may include providing a substrate. The non-conductive layer may be positioned relative to a substrate. The substrate may be monitored with the sensor device. A status of the substrate may be determined through changes in the conductive layer.

Variation 16 may include the method of variation 15 wherein determining the status of the substrate may include determining a deformation of the substrate by detecting the presence of a factor that deforms the substrate.

Variation 17 may include the method of variation 11 and may include measuring an opposition to current in the conductive layer; and may include comparing at least one of a magnitude of the opposition or a rate of change of the opposition to known values. A characteristic of the deformation may be determined from the comparison.

Variation 18 may include the method of variation 11 and may include subjecting the non-conductive layer to a variable causing a deformation. The deformation may be detected through a resulting change in an opposition to current in the conducting layer.

Variation 19 may include the method of variation 11 and may include providing an array of the sensor devices; monitoring the array; and evaluating differences in an opposition to a current at individuals of the sensor devices in the array to determine a location of the deformation.

Variation 20 may involve a method that may include providing a substrate. A sensor device may be coupled to the substrate and may include a non-conductive layer and a conductive layer overlying the non-conductive layer. The sensor device may be constructed and arranged to measure or monitor at least one variable in the substrate, or a change in an opposition to current in the conductive layer to provide measurement or monitoring of the at least one variable based on at least one calculation.

The above description of select variations within the scope of the invention is merely illustrative in nature and, thus, variations or variants thereof are not to be regarded as a departure from the spirit and scope of the invention.

What is claimed is:
1. A method comprising:
 forming a substrate as part of a battery;
 providing a non-conductive layer; providing a conductive layer and overlying the non-conductive layer with the conductive layer to form a sensor device;
 positioning the sensor device in contact with the substrate;
 evaluating a quality of an environment within which the sensor device is disposed by monitoring an opposition to electrical current through the conductive layer;

determining the location of a status of the non-conductive layer or of the conductive layer through a change in the opposition;

determining whether a change in the quality of the environment has occurred by evaluating changes in the opposition to the electrical current; and indicating electrolyte decomposition of the battery by the change in quality of the environment, wherein the change in quality of the environment comprises expansion of the substrate.

2. The method of claim 1 comprising;
providing a number of conductive leads electrically coupled with the conductive layer;
extending the conductive leads to run parallel to one another across the non-conductive layer;
varying a spacing distance between the conductive leads; and
detecting multiple thresholds of changes in the quality by separately monitoring the conductive leads with varying spacing.

3. The method of claim 1 comprising:
electrically coupling a number of conductive leads to the non-conductive layer;
varying a contact resistance between individual conductive leads and the non-conductive layer;
passing the electrical current through the conductive leads and into the conductive layer; and
detecting multiple thresholds of changes in the quality by separately monitoring the individual conductive leads with varying contact resistance.

4. The method of claim 1 comprising:
determining the status of the substrate through the changes in the opposition.

5. The method of claim 4 wherein the substrate expands when exposed to an increasing concentration of a constituent of the environment.

6. The method according to claim 5 comprising providing an array of sensor devices; monitoring the array; and evaluating differences in the opposition at individuals of the sensor devices in the array to determine a location of the deformation.

7. The method of claim 1 comprising providing a number of leads each electrically coupled with the conductive layer in various locations; and determining the location of a change in the status by measuring the opposition to current through the conductive layer from each of the number of leads.

8. The method of claim 1 comprising measuring the opposition to the current; and determining whether an event outside a selected range is occurring by comparing a rate of change of the opposition to known values of the opposition within the selected range.

9. The method of claim 1 comprising monitoring temperature; and correcting the opposition for temperature changes using the monitored temperature.

10. A method comprising:
forming a substrate as part of a battery;
forming a non-conductive layer of a material that does not conduct electricity;
positioning the non-conductive layer to monitor a potential deformation of a substrate;
forming a conductive layer;
overlying at least a part of the non-conductive layer with the conductive layer to form a sensor device;
monitoring for a deformation of at least one of the non-conductive layer and the substrate;
determining an occurrence of the deformation by monitoring for changes in opposition to current in the conductive layer indicative of factors that deform the substrate, wherein the factors comprise an electrolyte decomposition, a state of health of a battery and a state of charge of the battery;
detecting, by the changes in opposition, a variation in chemical concentration by the deformation in response to exposure of the substrate to the variation;
measuring a rate of the deformation; and
discriminating, by comparing the rate of the deformation to known values, between the electrolyte decomposition, the state of health and the state of charge as a source of the deformation.

11. The method of claim 10 comprising identifying multiple changes in the opposition; and determining a location of the deformation by comparing the multiple changes.

12. The method of claim 10 comprising providing a number of leads electrically coupled with the conductive layer; passing electrical current through the leads and into the conductive layer; and monitoring for the changes in opposition to the current passing through the conductive layer.

13. The method of claim 12 comprising determining a location of the deformation, including providing a variation between individuals of the leads and the conductive layer; measuring the opposition to current through the conductive layer from each of the number of leads; and comparing the measurements to determine the location.

14. The method of claim 10 comprising determining, from the monitoring, a status of the substrate through the changes in opposition.

15. The method according to claim 10 comprising subjecting the non-conductive layer to a variable causing a deformation; and detecting the deformation through a resulting change in an opposition to current in the conducting layer.

16. The method according to claim 10 comprising providing an array of the sensor devices; monitoring the array; and evaluating differences in an opposition to a current at individuals of the sensor devices in the array to determine a location of the deformation.

* * * * *